(12) United States Patent
Blank et al.

(10) Patent No.: US 8,912,240 B2
(45) Date of Patent: Dec. 16, 2014

(54) PRODUCTION OF METHANOL AND ETHANOL FROM CO OR $CO_2$

(71) Applicant: Eastman Chemical Company, Kingsport, TN (US)

(72) Inventors: Jan Hendrik Blank, Doha (QA); David John Cole-Hamilton, St. Andrews (GB); Robert Thomas Hembre, Johnson City, TN (US); James Allen Ponasik, Jr., Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 29 days.

(21) Appl. No.: 13/774,475

(22) Filed: Feb. 22, 2013

(65) Prior Publication Data
US 2014/0243435 A1 Aug. 28, 2014

(51) Int. Cl.
C07C 27/00 (2006.01)
C07C 29/157 (2006.01)

(52) U.S. Cl.
CPC .................................. *C07C 29/157* (2013.01)
USPC ......................................... 518/700; 518/715

(58) Field of Classification Search
CPC ...... C07C 31/04; C07C 31/08; C07C 29/157; B01J 31/0268; B01J 2231/62; B01J 2231/625
USPC ................................................. 518/700, 715
See application file for complete search history.

(56) References Cited

U.S. PATENT DOCUMENTS

| | | | |
|---|---|---|---|
| 2,535,060 A | 12/1950 | Gresham | |
| 2,549,470 A | 4/1951 | Howk et al. | |
| 3,285,948 A | 11/1966 | Butter | |
| 3,565,823 A | 2/1971 | Parshall | |
| 4,014,913 A | 3/1977 | Ellgen et al. | |
| 4,265,828 A | 5/1981 | Knifton | |
| 4,270,015 A | 5/1981 | Knifton | |
| 4,301,253 A | 11/1981 | Warren | |
| 4,315,994 A | 2/1982 | Knifton | |
| 4,323,513 A | 4/1982 | Dombek | |
| 4,332,914 A | 6/1982 | Knifton | |
| 4,332,915 A | 6/1982 | Knifton et al. | |
| 4,339,545 A | 7/1982 | Knifton | |
| 4,362,821 A | 12/1982 | Lin | |
| 4,362,822 A | 12/1982 | Knifton | |
| 4,366,259 A | 12/1982 | Knifton et al. | |
| 4,396,726 A | 8/1983 | Simons | |
| 4,421,862 A | 12/1983 | Bradley | |
| 4,451,679 A | 5/1984 | Knifton et al. | |
| 4,463,105 A | 7/1984 | Ichikawa et al. | |
| 4,518,715 A | 5/1985 | Knifton | |
| 4,525,481 A | 6/1985 | Lin et al. | |
| 4,556,744 A * | 12/1985 | Griggs et al. ................. 568/487 |
| 4,558,072 A | 12/1985 | Grigsby, Jr. et al. | |
| 4,569,948 A | 2/1986 | Ono et al. | |
| 4,584,322 A | 4/1986 | Smith | |
| 4,605,677 A | 8/1986 | Knifton | |
| 4,618,628 A | 10/1986 | Head et al. | |
| 4,622,343 A | 11/1986 | Knifton et al. | |
| 4,703,064 A | 10/1987 | Dombek | |
| 4,954,665 A | 9/1990 | Vidal | |
| 5,869,739 A | 2/1999 | Ikariya et al. | |
| 6,916,951 B2 | 7/2005 | Tustin et al. | |
| 7,608,743 B2 | 10/2009 | Olah et al. | |
| 2013/0225873 A1* | 8/2013 | Blank et al. ................... 568/840 |

FOREIGN PATENT DOCUMENTS

| | | |
|---|---|---|
| DE | 10 2009 037884 A1 | 3/2010 |
| EP | 0 013 008 A1 | 7/1980 |
| EP | 0 075 937 A1 | 4/1983 |
| GB | 2 024 811 A | 1/1980 |
| GB | 2 106 511 A | 4/1983 |
| JP | 58-172332 A | 10/1983 |
| JP | 7-017884 A | 1/1995 |
| JP | 8-067645 A | 3/1996 |
| JP | 3 108 714 B2 | 11/2000 |
| JP | 3 146 216 B2 | 3/2001 |
| JP | 3 614 449 B2 | 11/2004 |
| JP | 3 702 343 B2 | 10/2005 |

OTHER PUBLICATIONS

B.D. Dombek, "A Novel Catalytic System for Homogeneous Hydrogentation of Carbon Monoxide: Ruthenium Complexes in the Presence of Iodide Promoters," J. Am. Chem. Soc., vol. 103, pp. 6508-6510 (1981).
J.F. Knifton et al., "Syngas Reactions. Aliphatic Alcohols and Esters from Synthesis Gas," Organometallics, vol. 3, pp. 62-69 (1984).
H. Ono et al., "Promotion Effect of Mixed Halides on Homogeneous Ruthenium Catalysis in Direct Synthesis of Ethanol from Hydrogen and Carbon Monoxide," J. Mol. Catal., vol. 57, pp. 113-123 (1989).
J.F. Knifton, "The Selective Generation of Acetic Acid Directly from Synthesis Gas," ACS Symp. Ser., vol. 328, pp. 98-107 (1987).
J.F. Knifton, "Ethylene Glycol from Synthesis Gas via Bimetallic Catalysis," J. Chem. Soc., Chem. Comm., pp. 729-730 (1983).
J.F. Knifton, "Ethylene Glycol from Synthesis Gas via Ruthenium Melt Catalysis," J. Am. Chem. Soc., vol. 103, pp. 3959-3961 (1981).
J.F. Knifton, "Vicinal Glycol Esters from Synthesis Gas," J. Chem. Soc., Chem. Comm., pp. 188-189 (1981).
M.R. Netherton et al., "Air-Stable Trialkylphosphonium Salts: Simple, Practical, and Versatile Replacements for Air-Sensitive Trialkylphosphines. Applications in Stoichiometric and Catalytic Processes," Org. Ltr., vol. 3, pp. 4295-4298 (2001).
S. Yoshida et al., "Hydrogenation of Carbon Monoxide by Ruthenium Catalysts: A Synergistic Effect of Chloride Salts and Weak Acids," J. Mol. Catal., vol. 42, pp. 215-227 (1987).

(Continued)

*Primary Examiner* — Jafar Parsa
(74) *Attorney, Agent, or Firm* — Phan Law Group PLLC

(57) ABSTRACT

This invention relates to a process for making methanol and ethanol from carbon dioxide and hydrogen. The process includes contacting a mixture of carbon dioxide and hydrogen with a catalyst system containing a ruthenium compound—and optionally, a chloride or bromide-containing compound—dispersed in a low-melting tetraorganophosphonium chloride or bromide salt under conditions effective to produce methanol and ethanol. The invention also relates to a process for making methanol and ethanol from carbon monoxide and water using the same catalyst system.

24 Claims, 3 Drawing Sheets

(56) References Cited

OTHER PUBLICATIONS

H. Ono et al., "Hydrogenation of Carbon Monoxide with Homogeneous Ruthenium Catalysts: Novel Effect of Phosphoric Acid on Ethanol Synthesis," J. Mol. Catal., vol. 58, pp. 289-297 (1990).

C.A. Huff et al., "Cascade Catalysis for the Homogeneous Hydrogenation of CO2 to Methanol," J. Am. Chem. Soc., vol. 133, pp. 18122-18125 (2011).

T. Inui et al. "Highly effective synthesis of ethanol by CO2-hydrogenation on well balanced multi-functional FT-type composite catalysts," Applied CAT. A: General, vol. 186 pp. 395-406 (1999).

T. Inui, "Effective Conversion of CO2 to Valuable Compounds by Using Multifunctional Catalysts," CO2 Conversion and Utilization, ACS Symposium Series 809, Chapter 9, pp. 130-152 (2002).

S. Werner et al., "Homogeneous ruthenium-based water-gas shift catalysts via supported ionic liquid phase (SILP) technology at low temperature and ambient pressure," Phys. Chem. Chem Phys., vol. 11, pp. 10817-10819 (2009).

V. Gronemann et al., "CO2 based methanol ready for industrial scale," Nitrogen and Syngas, vol. 36, pp. 1-4 (2010).

English Abstract of DE 10 2009 037884 A1, 2009.

English Abstract of JP 58-172332 A (1983).

U.S. Appl. No. 13/594,537, filed Aug. 24, 2012.

English Abstract of JP 7-017884 A (1995).

English Abstract of JP 8-067645 A (1996).

P.C. Ford et al., "Nucleophilic Activation of Carbon Monoxide: Applications to Homogeneous Catalysis by Metal Carbonyls of the Water Gas Shift and Related Reactions," Adv. Organomet. Chem., vol. 28, pp. 139-217 (1988).

Bulletin of the Academy of Sciences, USSR, p. 2329 (1972).

M. Cho, "Coherent Two-Dimensional Optical Spectroscopy," Chem. Rev., vol. 108, pp. 1331-1418 (2008).

V.K. Srivastava et al., "Ruthenium carbonyl-complex catalyzed hydroaminomethylation of olefins with carbon dioxide and amines," Catal. Commun., vol. 10, pp. 1791-1795 (2009).

K. Tominaga et al., "Ruthenium Complex Catalysed Hydrogenation of Carbon Dioxide to Carbon Monoxide, Methanol and Methane," J. Chem. Soc., Chem. Commun., pp. 629-631 (1993).

J. Wasilke et al., "Concurrent Tandem Catalysis," Chem. Rev., vol. 105, pp. 1001-1020 (2005).

Y. Inoue et al., "Catalytic Fixation of Carbon Dioxide to Formic Acid by Transition-Metal Complexes Under Mild Conditions," Chem. Lett., Chem. Soc. Japan, pp. 863-864 (1976).

K. Tominaga et al., "Reverse Water-Gas Shift Reaction Catalyzed by Ruthenium Cluster Anions," Chem. Lett., Chem. Soc. Japan, pp. 1391-1394 (1994).

H.S. Muralidhara, "Enhance sparations with electricity," Chemtech, pp. 36-41 (May 1994).

B. Doss et al., "Optimization of Methanol Synthesis from Carbon Dioxide and Hydrogen: Demonstration of a Pilot-Scale Carbon-Neutral Synthetic Fuels Process," Energy & Fuels, vol. 23, pp. 4647-4650 (2009).

J.S. Bradley, "Homogeneous Carbon Monoxide Hydrogenation to Methanol Catalyzed by Soluble Ruthenium Complexes," J. Am. Chem. Soc., vol. 101, pp. 7419-7421 (1979).

D.J. Darensbourg et al., "Homogeneous Catalysts for Carbon Dioxide/Hydrogen Activation. Alkyl Formate Production Using Anionic Ruthenium Carbonyl Clusters as Catalysts," J. Am. Chem. Soc., vol. 105, pp. 5937-5939 (1983).

K. Tominaga et al., "Homogeneous Ru-Co bimetallic catalysis in CO2 hydrogenation: the formation of ethanol," J. Mol. Catal., vol. 89, pp. 51-56 (1994).

K. Tominaga et al., "Ruthenium-catalyzed one-pot hydroformylation of alkenes using carbon dioxide as a reactant," J. Mol. Catal. (A), vol. 220, pp. 159-165 (2004).

H. Ono et al., "Selective synthesis of acetic acid from hydrogen and carbon monoxide by homogeneous bimetallic catalysts," J. Organomet. Chem., vol. 331, pp. 387-395 (1987).

K. Tominaga et al., "Methanol homologation using carbon dioxide catalyzed by ruthenium-cobalt bimetallic complex system," Studies in Surface Science and Catalysis, vol. 114, pp. 495-498 (1998).

E. Balaraman et al., "Unprecedented Catalytic Hydrogenation of Urea Derivatives to Amines and Methanol," Angew. Chem. Int. Ed., vol. 50, pp. 11702-11705 (2011).

K. Tominaga et al., "Homogeneous Hydrogenation of Carbon Dioxide to Methanol Catalyzed by Ruthenium Cluster Anions in the Presence of Halide Anions," Bull. Chem. Soc. Jpn., vol. 68, 2837-2842 (1995).

R.M. Laine et al., "Homogeneous Catalysis by Ruthenium Carbonyl in Alkaline Solution: the Water Gas Shift Reaction," J. Am. Chem. Soc., Comm. Ed., vol. 99, pp. 252-253 (1977).

International Search Report and Written Opinion issued in Int'l Application No. PCT/US2014/013095, pp. 1-10 (May 23, 2014).

* cited by examiner

PRODUCTION OF METHANOL AND ETHANOL FROM CO OR CO₂

FIELD OF THE INVENTION

The invention generally relates to processes for making methanol and ethanol. In particular, in one aspect, the invention relates to the catalyzed hydrogenation of carbon dioxide to form methanol and ethanol. In another aspect, the invention relates to the catalyzed reaction of carbon monoxide with water to form methanol and ethanol.

BACKGROUND OF THE INVENTION

The conversion of either carbon monoxide or carbon dioxide into derivatives with a C—C bond is an important first step in developing technology for producing organic chemicals from these $C_1$ feedstocks. Due to its low reactivity, carbon dioxide poses a particular challenge, yet an important one, to achieve efficient utilization of many carbon feedstocks in large-scale fuel or commodity chemical production. An emphasis on carbon dioxide utilization has inspired development of $CO_2$-to-methanol technologies.

One approach uses promoted Cu/ZnO heterogeneous catalyst systems similar to current commercial methanol technologies. The reaction proceeds according to Equation (1) below:

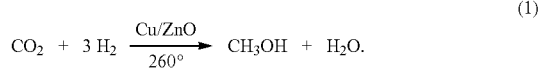

(1)

Relevant to an understanding of such $CO_2$ hydrogenation catalysis is the water-gas-shift (WGS) reaction according to Equation (2) below:

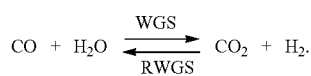

(2)

The WGS reaction is reversible and is catalyzed by many different transition metals. It is used on an industrial scale for hydrogen generation in ammonia and methanol synthesis. Such practice uses metal oxide catalysts in a two-step, high (T>350° C.) and low (210-240° C.) temperature, process. Homogeneous catalysts for the WGS reaction show significant activity at much lower temperatures (60-160° C.).

But it is the opposite reaction, referred to as the "reverse water-gas-shift" (RWGS) reaction, that is germane to $CO_2$ hydrogenation. The RWGS reaction is considered the first step of the process depicted in Equation (1), i.e., the conversion of $CO_2$ to CO. The CO is then hydrogenated to form methanol.

The $CO_2$-to-methanol process according to Equation (1) accomplishes two chemical steps in a single reactor, with a single catalyst system: RWGS and methanol synthesis. The term "tandem catalysis" has been coined to describe such processes, and examples where both chemical steps are catalyzed by the same catalyst system are referred to as "concurrent tandem cataylsis."

In one aspect, the present invention aims to execute three chemical steps in a single unit operation and, thus, might be referred to as "double-tandem" catalysis: RWGS reaction; methanol synthesis; and methanol homologation to ethanol, all in a single step with the stoichiometry described in Equation (4) below:

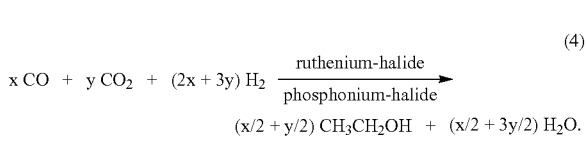

(4)

Demanding aspects of "double-tandem" catalysis are that all three reactions should occur at generally the same conditions of temperature and pressure, the products of one reaction should be acceptable as reactants for the next (twice), and the promoters or co-catalysts for one reaction should not be poisons (or ideally, they would also be activators) for the subsequent reactions.

JP 3,614,449 B2 (Tominaga et al., 2004) discloses the conversion of carbon dioxide to ethanol using a ruthenium-cobalt-iodide catalyst system in a pyrrolidone or imidazolidinone solvent. JP '449, however, neither claims nor observes concurrent conversion of carbon monoxide feedstock. JP '449 also does not disclose using a molten salt as the reaction solvent.

In another aspect, the present invention aims to produce methanol and ethanol by reacting carbon monoxide with water.

The present invention addresses these as well as other objects, which will become apparent from the following description and the appending claims.

SUMMARY OF THE INVENTION

The invention is as set forth in the appended claims.

Briefly, the present invention provides processes for preparing methanol and ethanol. In one embodiment, the process comprises contacting a mixture of carbon dioxide and hydrogen with a catalyst system comprising a ruthenium compound (and optionally, a chloride or bromide-containing compound) dispersed in a low-melting tetraorganophosphonium chloride or bromide salt under conditions effective to produce methanol and ethanol.

In another embodiment, the process comprises contacting a mixture of carbon monoxide and water with a catalyst system comprising a ruthenium compound and a chloride or bromide-containing compound dispersed in a low-melting tetraorganophosphonium chloride or bromide salt under conditions effective to produce methanol and ethanol.

DETAILED DESCRIPTION OF THE INVENTION

Figure 1:
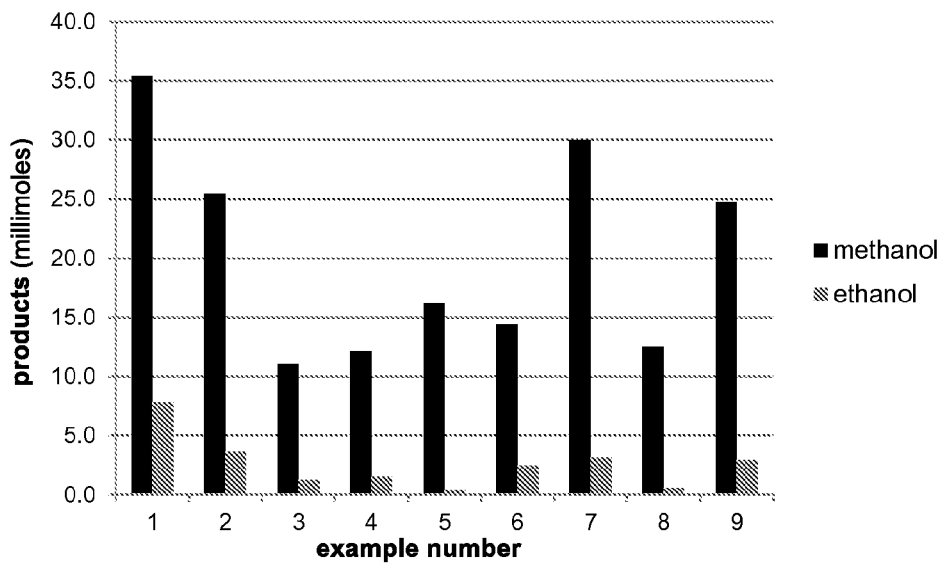
FIG. 1 is a bar graph of the amounts of methanol and ethanol produced in Examples 1-9. The x-axis shows the example numbers. The y-axis shows the amounts of methanol and ethanol in millimoles.

It has been surprisingly discovered that ruthenium, with or without additional co-catalysts, and a halide-containing ionic liquid (i.e., a molten salt), as a solvent, can hydrogenate $CO_2$ or $CO_2$-containing mixtures to produce $C_2$-oxygenate products such as ethanol or acetic acid coincident with the production of methanol or its derivatives. The low-volatility of the molten salt is of particular value in separating the relatively volatile products from the reaction mixture.

The catalyst system for the process according to the invention comprises a ruthenium compound dispersed in a low-melting tetraorganophosphonium chloride or bromide salt.

The ruthenium catalyst component may be chosen from a wide variety of organometallic or inorganic compounds, complexes, etc. For instance, the ruthenium component may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, anhydrous ruthenium(III) chloride, and ruthenium nitrate; or as the salt of a suitable organic carboxylic acid, for example, ruthenium(III) acetate, ruthenium propionate, and ruthenium(III) acetylacetonate. The ruthenium component may also be added to the reaction zone as a carbonyl or hydrocarbonyl derivative. Suitable examples include triruthenium dodecacarbonyl; hydrocarbonyls such as $H_2Ru_4(CO)_{13}$, $H_4Ru_4(CO)_{12}$, and salts of $[HRu_3(CO)_{11}]^-$; and substituted carbonyl species such as the tricarbonylruthenium(II) chloride dimer, $[Ru(CO)_3Cl_2]_2$, and salts of $[Ru(CO_3)X_3]^-$ where X=Cl or Br. Any other ruthenium compound that can generate a soluble ruthenium carbonyl halide complex under the reaction conditions can also be used. The ruthenium compounds can be used individually or as mixtures of two or more ruthenium compounds.

Preferred ruthenium compounds include oxides of ruthenium, ruthenium salts of a mineral acid, ruthenium salts of an organic carboxylic acid, and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, triruthenium dodecacarbonyl, bis[ruthenium(tricarbonyl)dichloride], and bis[ruthenium(tricarbonyl)dibromide].

The ruthenium compound can be used in an amount ranging from 0.01 to 30 weight percent of ruthenium, based on the total weight of the reaction mixture. The concentration of ruthenium in the reaction mixture is preferably from 0.2 to 10 weight percent and, more preferably, from 0.5 to 5 weight percent.

The catalyst system may optionally further include a chloride or bromide-containing compound as a promoter.

The chloride or bromide-containing compound that may be used in the catalyst system is not particularly limiting. Practically any source of Cl or Br can be used. Examples of such a source include elemental chlorine and bromine, as well as HCl and HBr. Also among the useful compounds are the alkyl halides having, for example, from 1 to 10 carbon atoms, as well as any other organic chloride or bromide compound. Illustrative of suitable chloride or bromide promoters include methyl chloride, butyl chloride, acetyl chloride, hydrogen chloride, cobalt chloride, as well as the corresponding bromide compounds. Further, mixtures of the elemental halogens and/or the halogen compounds can be used.

A preferred class of chloride or bromide-containing promoters includes a triorganophosphonium salt having the general formula (II)

$$[R_1R_2R_3PH][X^2] \qquad (II)$$

wherein $R_1$, $R_2$, and $R_3$ are each independently selected from $C_1$-$C_{24}$ alkyl or aryl hydrocarbon groups or functionalized alkyl or aryl groups containing ether, alcohol, ketone, carboxylic acid or ester, amine, amide, thioether, phosphine oxide, nitrile, heteroaromatic, or fluorocarbon groups; and $X^2$ is chloride or bromide.

Illustrative examples of suitable triorganophosphonium salts include tributylphosphonium chloride, triphenylphosphonium chloride, tributylphosphonium bromide, and triphenylphosphonium bromide.

The preferred salts are generally the trialkylphosphonium salts containing alkyl groups having 1-6 carbon atoms, such as methyl, ethyl, and butyl. Tributylphosphonium salts, such as tributylphosphonium chloride, are most preferred for the practice of this invention.

The chloride or bromide-containing promoter can be charged to the reaction in an amount sufficient to increase production of methanol or ethanol compared to a catalyst system without the halogen-containing compound. Typically, the halogen promoter can be used in an amount sufficient to produce a promoter/Ru atom molar ratio of 0.05:1 to 3.5:1 during the reaction. Other exemplary molar ratios include 0.05:1 to 3:1, 0.1:1 to 2.5:1, 0.05:1 to 1:1, 0.1:1 to 0.9:1, and 0.2:1 to 0.8:1. When a triorganophosphonium salt is used, a triorganophosphonium salt to Ru atom molar ratio of 0.2:1 to 0.6:1 is preferred.

In certain embodiments, the catalyst system for use in the present invention is free or essentially free of iodide or iodine-containing compounds as co-catalysts/promoters.

According to the invention, the catalyst components are dispersed in a low-melting tetraorganophosphonium salt. By "low melting," it is meant that the salt melts at a temperature less than the reaction temperature for making the methanol and ethanol. Usually, the salt has a melting point of 180° C. or less, and preferably of 150° C. or less.

The low-melting tetraorganophosphonium salt can have the general formula (I):

$$[R_1R_2R_3R_4P][X^1] \qquad (I)$$

wherein $R_1$, $R_2$, $R_3$, and $R_4$ are each independently selected from $C_1$-$C_{24}$ alkyl or aryl hydrocarbon groups or functionalized alkyl or aryl groups containing ether, alcohol, ketone, carboxylic acid or ester, amine, amide, thioether, phosphine oxide, nitrile, heteroaromatic, or fluorocarbon groups; and $X^1$ is chloride or bromide.

Illustrative examples of suitable tetraorganophosphonium salts include tetrabutylphosphonium chloride, heptyltriphenylphosphonium chloride, tetrabutylphosphonium bromide, and heptyltriphenylphosphonium bromide.

The preferred salts are generally the tetraalkylphosphonium salts containing alkyl groups having 1-6 carbon atoms, such as methyl, ethyl, and butyl. Tetrabutylphosphonium salts, such as tetrabutylphosphonium chloride, are most preferred for the practice of this invention.

The catalyst system according to the invention may be referred to as homogeneous since the catalyst components are typically dissolved or suspended in the molten salt under reaction conditions.

As noted, the catalyst system according to the invention is particularly suitable for preparing methanol and ethanol from carbon dioxide and hydrogen.

The reaction conditions effective to produce methanol and ethanol include a temperature from 100° C. to 350° C. Preferably, the temperature is at least 120° C., such as from 120° C. to 250° C. More preferably, the temperature is at least 150° C., such as from 150° C. to 220° C.

The effective reaction conditions also include a $CO_2/H_2$ pressure from 3 MPa to 70 MPa or more. Preferably, the $CO_2/H_2$ pressure ranges from 5 MPa to 40 MPa. More preferably, the $CO_2/H_2$ pressure ranges from 7 MPa to 25 MPa.

The carbon dioxide and hydrogen can be from any source. They can be introduced into the reactor separately or as a mixture. Thus, as used herein, the expression "a mixture of carbon dioxide and hydrogen" includes the possibility of introducing the carbon dioxide and the hydrogen separately or together into the reactor. The volumetric ratio of carbon dioxide to hydrogen ($CO_2:H_2$) introduced into the reactor can range from 0.1:1 to 1:1.

The gases introduced into the reactor may also include carbon monoxide.

The volumetric ratio of carbon monoxide to carbon dioxide ($CO:CO_2$) introduced into the reactor can range from 0.01:1 to 100:1.

The reaction may be carried out in the presence of methanol. Without wishing to be bound by theory, methanol may act as a reaction intermediate and increase the production of ethanol. If added, the methanol concentration may range from 0.01 to 10 mol/L, 0.1 to 5 mol/L, or 0.5 to 2 mol/mL in the reaction medium.

The hydrogenation of carbon dioxide is preferably carried out in the absence of added water, to maximize the production of ethanol.

The carbon dioxide and hydrogen are typically introduced into the reactor as gases, while the catalyst components are typically first introduced into the reactor as solids and/or liquids. Under reaction conditions, the tetraorganophosphonium salt should be in the liquid phase as a melt, and the ruthenium and chloride or bromide-containing compounds are dispersed in that melt.

The catalyst system according to the invention is also particularly suitable for preparing methanol and ethanol from carbon monoxide and water.

The reaction of carbon monoxide with water may be carried out using the same general conditions and parameters as described above in relation to the hydrogenation of carbon dioxide, to form the same products. The reaction of carbon monoxide with water may be carried out in the presence of hydrogen. Preferably, however, the reaction is carried out in the absence of added hydrogen. Moreover, water is typically introduced into the reactor as a liquid, while carbon monoxide is introduced as a gas.

The molar ratio of carbon monoxide to water introduced into the reactor may range from 3:1 to 2:3. Preferably, the molar ratio is around 3:2 (CO/water).

The processes of this invention can be conducted in a batch, semi-continuous, or continuous fashion. The catalyst system may be initially introduced into the reaction zone batchwise, or it may be continuously or intermittently introduced into such a zone during the course of the synthesis reaction. Operating conditions can be adjusted to optimize the formation of the desired alkanol product. Preferred products include methanol or ethanol or both. Other $C_2$-oxygenates may also be formed such as acetic acid and ethylene glycol. The alkanol product may be recovered by methods well known in the art, such as distillation, fractionation, extraction, and the like. A fraction rich in the ruthenium catalyst component may then be recycled to the reaction zone, if desired, and additional products generated. Additionally, methanol may be recovered and recycled to the reaction zone.

As used herein, the indefinite articles "a" and "an" mean one or more, unless the context clearly suggests otherwise. Similarly, the singular form of nouns includes their plural form, and vice versa, unless the context clearly suggests otherwise.

As used herein, the terms "synthesis gas" or "syngas" refer to a gas mixture of carbon monoxide (CO) and hydrogen ($H_2$).

While attempts have been made to be precise, the numerical values and ranges described herein should be considered to be approximations. These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to include all values within the range including sub-ranges such as 60 to 90 and 70 to 80.

This invention can be further illustrated by the following examples of preferred embodiments thereof, although it will be understood that these examples are included merely for purposes of illustration and are not intended to limit the scope of the invention. Unless otherwise indicated, all percentages are by weight, and the ratios of gases are based on volume.

EXAMPLES

Unless stated otherwise, all chemicals were obtained from Sigma Aldrich and used as received. Air-sensitive compounds were handled under $N_2$ using standard Schlenk techniques. NMR spectra where recorded on a Varian 300 NMR or Bruker AM 300/400 NMR spectrometers. The $^1H$ chemical shifts were referenced to the solvent: $CD_2HCN$ δ 1.95 (p, J=2.5 Hz). The chemical shifts of absorptions in the $^{31}P$ NMR spectra were referenced to external $H_3PO_4$.

All reactions were carried out in a 100-mL Hastelloy C autoclave with overhead stirring, a back-pressure regulator for pressure control, and a heating block with temperature control provided by feedback via a thermocouple in the autoclave thermowell. A ballast vessel of 0.5 L volume, capable of withstanding pressures up to 33 MPa, provided a gas supply to maintain a constant pressure during reactions. The transfer of gas to the autoclave was monitored by a Bronkhorst mass flow controller, and the pressure of the ballast vessel was monitored at ten second intervals using a computerized Picolog system with the results stored on a computer for analysis.

For quantitation of liquid samples, a gas chromatography analysis was performed using a Supelcowax-10 Capillary Column (60 m×0.32 mm×1.0 μm film thickness) using an Agilent 6890N Network GC system equipped with a flame ionization detector. The identification of these products was carried out on an HP 6890 series GC system equipped with a HP 5973 mass selective detector. Both machines used 1 ml $min^{-1}$ helium carrier gas flow with the injector and detector temperatures set to 250° C. The temperature was programmed as follows: 50° C., hold 3 minutes, ramp 20° C.

min⁻¹, 150° C., hold 5 min, ramp 20° C. min-1, 220° C., hold 13 minutes. The split ratio was 1:100.

For quantitation of gas samples, analysis was performed on an Agilent 3000 micro Gas Chromatograph fitted with two columns and a backflush injector: Column A: a molsieve column (12 μm×320 μm×10 m) fitted with a PlotU precolumn (30 μm×320 μm×3 m); and Column B: a PlotU column (30 μm×320 μm×8 m) fitted with a PlotQ precolumn (10 μm×320 μm×1 m). In both columns, the carrier gas was argon. Injection occurred through a backflush injector operated at 130° C. and at 0.22 MPa and 0.21 MPa for columns A and B, respectively. The separation occurred at 75° C. and 120° C. constant temperature for columns A and B, respectively. Analysis was performed using a TCD detector. In a typical experiment, the off-gas of the reactor was partially vented through a Schlenk-flask fitted with a rubber seal to collect a sample of the gas. With a 20 mL syringe flushed with $N_2$, a 3 mL sample was withdrawn and then diluted to 20 mL with $N_2$. The sample was then injected onto the micro-GC using a special fitted connection. For the experiment with regular gas analyses at different time intervals, a small sample of the headspace gas was isolated under pressure during the experiment. This was then vented directly into the syringe and then further diluted using $N_2$ before injection. Determination of the gas phase composition occurred through comparison of the relative peak areas of each component and by determining separately the relative sensitivity of the detector to each component.

Example 1 (Comparative)

Standard with 1:1 $CO/H_2$

The clean and dry autoclave was assembled, and 14.502 g of [PBu₄]Br (42.74 mmol), 0.499 g of $Ru_3(CO)_{12}$ (2.33 mmol Ru), and 0.414 g of [HPBu₃]Br (1.47 mmol) were added to the autoclave.

The autoclave was pressurized to ~1 MPa with $CO/H_2$ (1:1), and then the pressure was released to ambient pressure to purge the autoclave. This step was repeated five times. The system was tested for leaks, the heater was switched off, and the system was left under pressure (17.0 MPa) overnight.

The following morning, the system was tested for leaks again. The heater and stirrer were then switched on. When the temperature reached 200° C., the time was noted, and the pressure was adjusted to 25.0 MPa with $CO/H_2$ (1:1). The Picolog data point was noted, the mass flow controller datalogger was switched on, and the stirring speed was increased to a setting of 9.

During the reaction, the pressure was kept constant at 25.0 MPa via the pressure controller and gas uptake monitored by the mass flow controller. Gas feed ($CO/H_2$, 1:1) was from the ballast vessel fitted with a pressure transducer. The Picolog recorded the pressure of the ballast vessel every 10 seconds.

After 4 hours, the heater was switched off, the stirring was reduced, and the taps were closed. When the temperature was below 30° C., the autoclave was vented.

After venting, the autoclave was opened and inspected. The product mixture was a red liquid, which was analyzed by IR spectroscopy and ¹H NMR, and a small sample was stored.

The remainder of the liquid was transferred to a flask and stripped of volatiles by vacuum distillation using temperatures up to 250° C. The volatiles were trapped in a liquid $N_2$ cold-trap. The contents of the cold-trap were diluted using 5 mL of 2% (v/v) acetonitrile/NMP stock solution and analyzed using GC. The total product amounts were calculated using the acetonitrile and NMP peaks as internal references. The results are reported in Table 1.

Example 2

Standard with 1:1 $CO/H_2$ but Substitute 10 MPa $CO_2$, Total Pressure same at 25 MPa The clean and dry autoclave was assembled, and 14.503 g of [PBu₄]Br (42.74 mmol), 0.500 g of $Ru_3(CO)_{12}$ (2.34 mmol Ru), and 0.415 g of [HPBu₃]Br (1.47 mmol) were added to the autoclave. The autoclave was pressurized to 1 MPa with $CO/H_2$ (1:1), and then the pressure was released to ambient pressure to purge the autoclave. This step was repeated five times. The autoclave was then charged with $CO/H_2$ (1:1) to 9.3 MPa of pressure and left overnight.

The following morning, the system was checked for leaks, and the heater and stirrer were switched on. When the temperature reached 200° C., the pressure inside the autoclave was reduced to 14.0 MPa, and $CO_2$ was added until the pressure was 24.0 MPa. Next, $CO/H_2$ (1:1) was added again until the pressure was 25.0 MPa. The Picolog datapoint was noted, and the mass flow controller datalogging was switched on. The stirring speed was increased to a setting of 9, and the pressure was adjusted to 25.0 MPa again. The remainder of the experiment was performed as in Example 1. The results are reported in Table 1.

Example 3 (Comparative)

Standard with 1:1 $CO/H_2$ but Substitute 10 MPa $N_2$, Total Pressure same at 25 MPa The clean and dry autoclave was assembled, and 14.502 g of [PBu₄]Br (42.74 mmol), 0.500 g of $Ru_3(CO)_{12}$ (2.34 mmol Ru), and 0.415 g of [HPBu₃]Br (1.47 mmol) were added to the autoclave. The autoclave was pressurized to 1 MPa with $CO/H_2$ (1:1), and then the pressure was released to ambient pressure to purge the autoclave. This step was repeated six times. The autoclave was then charged with $CO/H_2$ (1:1) to 9.3 MPa of pressure and left overnight.

The following morning, no pressure drop was observed. The heater and stirrer were switched on, and during the heat-up, the Picolog data recorder was also switched on. When the temperature reached 199° C., the pressure inside the autoclave was reduced to 5.0 MPa, and $N_2$ was added until the pressure was 15.0 MPa, followed by the addition of $CO/H_2$ (1:1) until the pressure was 25.0 MPa. The temperature was 200° C., the stirrer was switched to a setting of 9, and the time was noted. The Picolog datapoint was noted, and the mass flow controller datalogging was switched on. The pressure was again adjusted to 25.0 MPa, as above. The remainder of the experiment was performed as in Example 2. The results are reported in Table 1.

Example 4 (Comparative)

The clean and dry autoclave was assembled, and 14.503 g of [PBu₄]Br (42.74 mmol), 0.500 g of $Ru_3(CO)_{12}$ (2.336 mmol Ru), and 0.415 g of [HPBu₃]Br (1.47 mmol) were added to the autoclave. The autoclave was pressurized to 1 MPa with $CO/H_2$ (1:1), and then the pressure was released to ambient pressure to purge the autoclave. This step was repeated five times. The autoclave was then charged with $CO/H_2$ (1:1) to 15 MPa of pressure and left overnight.

The following morning, no pressure drop was observed. The heater, the stirrer, and the Picolog data recorder were switched on. When the temperature reached 199° C., gas was released until the autoclave contained 15.0 MPa. The stirrer was switched to a setting of 9, and the time was noted. The remainder of the reaction was performed as in Example 2. The results are reported in Table 1.

Examples 1 and 4 may be considered reference examples with Example 1 examining 1:1 $CO/H_2$ at 25.0 MPa in tetrabutylphosphonium bromide with $Ru_3(CO)_{12}$ as catalyst precursor (~0.02 M, 1.54 wt % Ru, 5.03 mol % Ru) and Example 4 being operated under the same conditions, but with a lower pressure of 1:1 $CO/H_2$ at 15.0 MPa. The products of hydrogenation are listed in Table 1. The amount of methanol and ethanol produced are depicted in the FIG. 1. In Example 2, 10.0 MPa of $CO_2$ replaced an equivalent pressure of syngas in Example 1. In Example 3, 10.0 MPa of $N_2$ replaced the $CO_2$ of Example 2.

From FIG. 1, it can be seen that Example 3, which was charged with 15 MPa of 1:1 $CO/H_2$ and 10 MPa of $N_2$, produced nearly the same amount of methanol and ethanol as Example 4, which had only the 15 MPa of 1:1 $CO/H_2$ and no $N_2$. In contrast, Example 2, which replaced the 10 MPa of $N_2$ in Example 3 with 10 MPa of $CO_2$, produced nearly as much methanol and ethanol as Example 1, which had 25 MPa of 1:1 $CO/H_2$. These results indicate that the $CO_2$ boosted the methanol and ethanol production (nearly as much as $CO/H_2$) when compared to Example 4.

Example 5

Reaction of $CO_2$ and $H_2$

The clean and dry autoclave was assembled, and 14.502 g of $[PBu_4]Br$ (42.734 mmol), 0.500 g of $Ru_3(CO)_{12}$ (2.34 mmol Ru), and 0.415 g of $[HPBu_3]Br$ (1.47 mmol) were added to the autoclave. The autoclave was pressurized to 1 MPa with gas, and then the pressure was released to ambient pressure to purge the autoclave. Synthesis gas, $CO/H_2$ (1:2), was used three times, and then $H_2$ was used four times to ensure complete removal of air.

The system was initially pressurized to 12 MPa with $H_2$, then heated to 50° C. The pressure was then adjusted to 12.6 MPa with $H_2$. Next, 6.0 MPa of $CO_2$ were added to produce a total pressure was 19.0. The system was tested for leaks, the heater was switched off, and the system was left under pressure overnight.

The following morning, the system was tested for leaks again. Then, the heater and stirrer were switched on. When the temperature reached 200° C., the time was noted, and the reaction was allowed to proceed for 4 hours. At the end of 4 hours, the heater was switched off, and the heating jacket was removed for swift cooling.

When the temperature reached 50° C., the pressure was 15.5 MPa. When the temperature was below 30° C., the autoclave was vented and a gas sample was taken for GC analysis. The results of the gas sample analysis are reported in Table 2.

After venting, the autoclave was opened and inspected. The product mixture was a red liquid, which was analyzed by IR spectroscopy and $^1H$ NMR. A small sample was stored.

The remainder of the liquid was transferred to a flask and stripped of volatiles by vacuum distillation using temperatures up to 250° C. The volatiles were trapped in a liquid $N_2$ cold-trap. The contents of the cold-trap were diluted using 5 mL of a 2% (v/v) acetonitrile/NMP stock solution and analyzed using GC. The total product amounts where calculated using the acetonitrile and NMP peaks as internal references. The results reported in Table 1.

Example 6 (Comparative)

Reaction of CO and $H_2$

The clean and dry autoclave was assembled, and 14.503 g of $[PBu_4]Br$ (42.74 mmol), 0.499 g of $Ru_3(CO)_{12}$ (2.33 mmol Ru), and 0.415 g of $[HPBu_3]Br$ (1.47 mmol) were added to the autoclave. The autoclave was sealed and pressurized to 1 MPa with $CO/H_2$ (1:2) three times, and then with pure CO to 1 MPa four times to ensure complete removal of air.

Next, the autoclave was pressurized to 3.2 MPa of CO before adding $CO/H_2$ (1:2) until the pressure was 12.6 MPa. The system was closed and tested for leaks. None were found. It was left overnight under this atmosphere with a net composition of 6.3 MPa of CO and 6.3 MPa of $H_2$.

The following morning, the system was tested for leaks again. Then, as in Example 5, the heater and stirrer were switched on. When the temperature reached 200° C., the time was noted, and the reaction was allowed to proceed for 4 hours. At the end of 4 hours, the heater was switched off, and the heating jacket removed for swift cooling.

When the temperature was below 30° C., the autoclave was vented, and a gas sample was taken for GC analysis. The results of the gas sample analysis are reported in Table 2.

The remainder of the liquid was transferred to a flask and treated as in Example 5. The amounts of product measured are reported in Table 1.

Example 7

Reaction of CO and $H_2O$

The clean and dry autoclave was assembled, and 14.502 g of $[PBu_4]Br$ (42.73 mmol), 0.500 g of $Ru_3(CO)_{12}$ (2.34 mmol Ru), and 0.415 g of $[HPBu_3]Br$ (1.47 mmol) were added to the autoclave. The autoclave was pressurized to 1 MPa with gas, and then the pressure was released to ambient pressure to purge the autoclave. Synthesis gas, $CO/H_2$ (1:2), was used three times, and then 4.3 mL of water was added by syringe under a positive flow of $CO/H_2$.

Next, the autoclave was pressurized to 3.3 MPa with CO, then heated to 50° C. The pressure was then adjusted to 3.2 MPa. After that, 9.4 MPa of CO were added to produce a total pressure of 12.6 MPa. The system was tested for leaks, the heater was switched off, and the system was left under pressure overnight.

The following morning, the system was tested for leaks again. Then, as in Example 5, the heater and stirrer were switched on. When the temperature reached 200° C., the time was noted, and the reaction was allowed to proceed for 4 hours. At the end of 4 hours, the heater was switched off, and the heating jacket removed for swift cooling.

When the temperature reached 50° C., the pressure was 13.5 MPa. When the temperature was below 30° C., the autoclave was vented, and a gas sample was taken for GC analysis. The results of the gas sample analysis are reported in Table 2.

After venting, the autoclave was opened and inspected. The product mixture was a red liquid containing a small amount of solid. The liquid was analyzed by IR spectroscopy and $^1H$ NMR. A small sample was stored.

The remainder of the liquid was transferred to a flask and treated as in Example 5. The amounts of product measured are reported in Table 1.

Example 8

Reaction of $CO/H_2$ and $H_2O$

The clean and dry autoclave was assembled, and 14.502 g of $[PBu_4]Br$ (42.73 mmol), 0.500 g of $Ru_3(CO)_{12}$ (2.34 mmol Ru), and 0.415 g of $[HPBu_3]Br$ (1.47 mmol) and water (4.3 mL) were added to the autoclave. The autoclave was pressurized to 1 MPa with $CO/H_2$ (1:2), and then the pressure was released to ambient pressure to purge the autoclave three times. Next the system was purged with CO four times to ensure the complete removal of air.

Next, the autoclave was warmed to 50° C., and the pressure was adjusted to 3.2 MPa of CO. The pressure was then adjusted up to 12.6 MPa with $CO/H_2$ (1:2). The system was tested for leaks. None were found. The heater was switched off, and the system was left under this atmosphere with a net composition of 6.3 MPa of CO and 6.3 MPa of $H_2$ overnight.

The following morning, the system was tested for leaks again. Then, as in Example 5, the heater and stirrer were switched on. When the temperature reached 200° C., the time was noted, and the reaction was allowed to proceed for 4 hours. At the end of 4 hours, the heater was switched off, and the heating jacket removed for swift cooling.

When the temperature reached 50° C., the pressure was 14.8 MPa. When the temperature was below 30° C., the autoclave was vented, and a gas sample was taken for GC analysis. The results of the gas sample analysis are reported in Table 2.

After venting, the autoclave was opened and inspected. The product mixture was a red liquid. The liquid was analyzed by IR spectroscopy and $^1H$ NMR. A small sample was stored.

The remainder of the liquid was transferred to a flask and treated as in Example 5. The amounts of product measured are reported in Table 1.

because the water has shifted much of the CO to $CO_2$ leaving a small partial pressure of CO (in contrast to Example 6) and shunting its production of ethanol.

Figure 2:
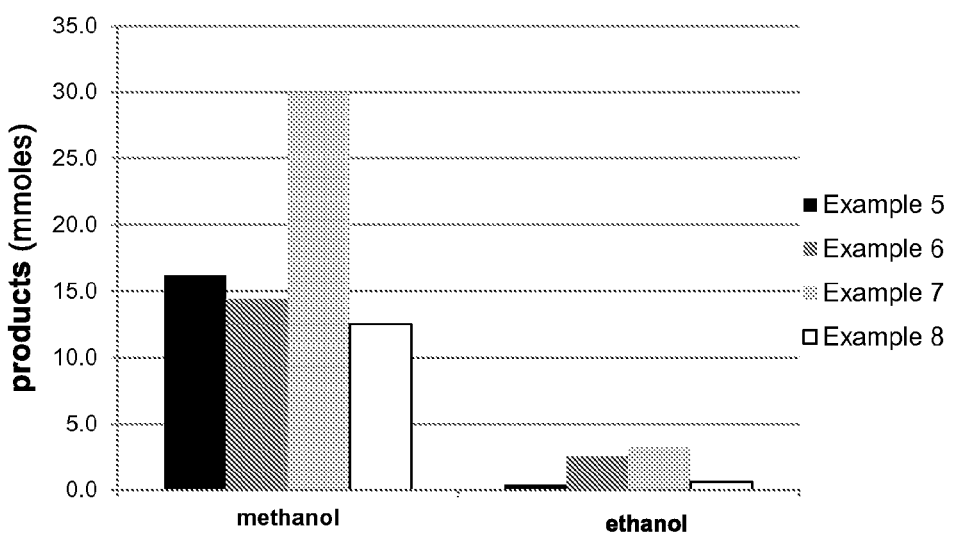
FIG. 2 is a bar graph of the amounts of methanol and ethanol produced in Examples 5-8. The x-axis shows the products methanol and ethanol. The y-axis shows the amounts of methanol and ethanol in millimoles.

FIG. 2 graphically depicts the amounts of methanol and ethanol produced in Examples 5-8.

Figure 3:
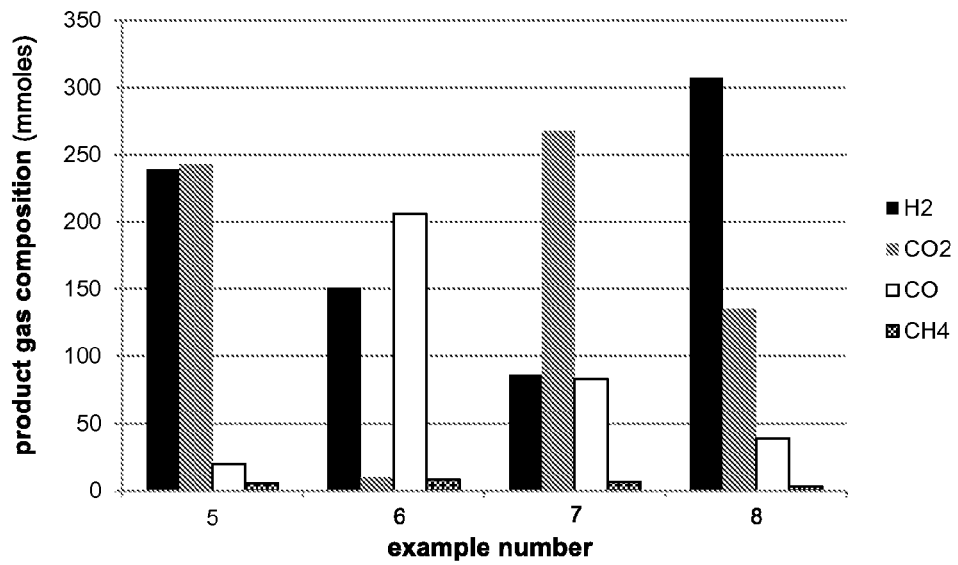
FIG. 3 is a bar graph of the amounts of the different species in the gas phase of the products in Examples 5-8. The x-axis shows the example numbers. The y-axis shows the amounts of the various species in millimoles.

FIG. 3 graphically depicts the gas-phase composition of the products from Examples 5-8.

Example 9

The Rate of Approach to Equilibrium in the Water-gas-shift Reaction

The clean and dry autoclave was assembled, and 14.502 g $[PBu_4]Br$ (42.74 mmol), 0.500 g $Ru_3(CO)_{12}$ (2.336 mmol Ru), 0.415 g of $[HPBu_3]Br$ (1.47 mmol), and 4.3 mL of water were added to the autoclave. The autoclave was sealed and purged 7 times using CO. The system was pressured to 13.0 MPa and checked for leaks. A small leak was found and fixed. After that, no leaks were detected. The system was left under pressure overnight.

Figure 4:
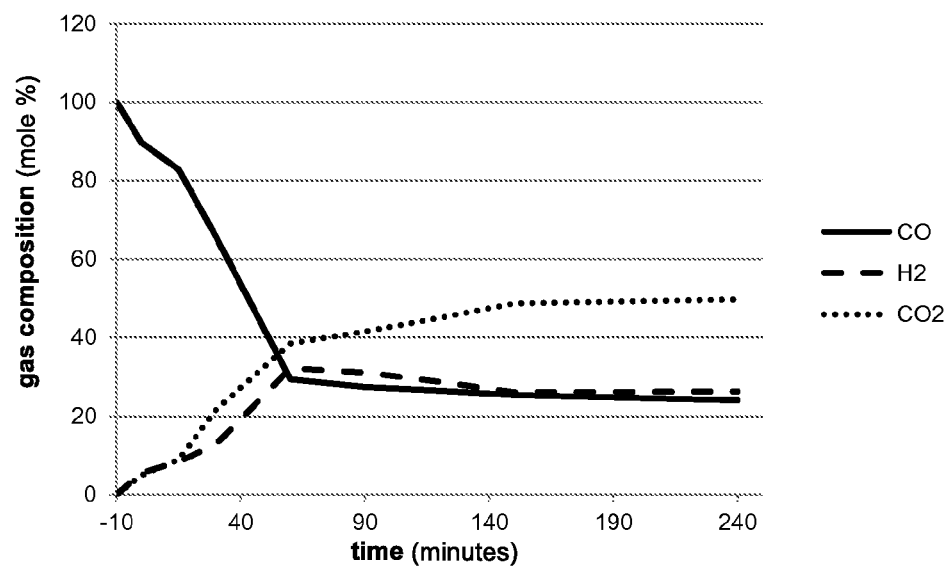
FIG. 4 is a bar graph of the composition profile (in mole%) versus time (in hours) of the gas-phase composition in Example 9.

The following morning, the autoclave was warmed to 50° C. and checked for leaks. None were found. The pressure was then reduced to 12.6 MPa. The heater and stirrer were switched on. During heat-up, a sample of the gas was taken for GC analysis. The temperature was approximately 150° C. When the temperature reached 200° C., the time was noted, and another gas sample was taken for GC analysis. Additional gas sampling occurred at 15, 30, 60, 90, 120, 180, and 240 minutes after the start of the reaction. The results of the gas sample analysis are reported in Table 3. The data in Table 3 is graphically depicted in FIG. 4.

After 4 hours, the heater was switched off. The reactor was cooled down to 30° C. When the temperature was 50° C., the pressure was measured to be 12.5 MPa. The remainder of the procedure was performed as in Example 5. The product mixture was a red liquid slush. The amounts of product measured are reported in Table 1.

TABLE 1

| Example No. | Products (mmoles) | | | | | | | |
|---|---|---|---|---|---|---|---|---|
| | MeOH | EtOH | PrOH | BuOH | AcOH | Ethylene Glycol | β-Methoxy-Ethanol | β-Ethoxy-Ethanol |
| 1 | 35.4 | 7.82 | 0.32 | 0.02 | 0.29 | 2.38 | 0.34 | 0.02 |
| 2 | 25.5 | 3.61 | 0.06 | 0.01 | 0.31 | 0.75 | 0.03 | — |
| 3 | 11.1 | 1.26 | 0.05 | 0.01 | — | 0.54 | 0.04 | — |
| 4 | 12.1 | 1.48 | 0.06 | 0.01 | — | 0.81 | 0.05 | — |
| 5 | 16.2 | 0.37 | 0.02 | 0.05 | 0.12 | 0.08 | 0.01 | 0.04 |
| 6 | 14.4 | 2.46 | 0.09 | 0.03 | 0.22 | 0.82 | 0.07 | 0.05 |
| 7 | 30.0 | 3.17 | 0.04 | 0.03 | 0.18 | 0.43 | 0.03 | 0.04 |
| 8 | 12.5 | 0.58 | — | 0.03 | 0.17 | — | 0.01 | 0.04 |
| 9 | 24.7 | 2.96 | — | 0.03 | 0.34 | 0.64 | 0.03 | 0.05 |

— = not detected

TABLE 2

| Example No. | | Gas-Phase Composition[a] (mmoles) | | | | |
|---|---|---|---|---|---|---|
| | | CO | $H_2O$[b] | $CO_2$ | $H_2$ | $CH_4$ |
| 5 | Reactants | 0 | 0 | 206 | 413 | — |
| | Products | 20 | — | 243 | 239 | 5 |
| 6 | Reactants | 206 | 0 | 0 | 206 | — |
| | Products | 176 | — | 10 | 151 | 8 |
| 7 | Reactants | 413 | 239 | 0 | 0 | — |
| | Products | 83 | — | 268 | 86 | 6 |
| 8 | Reactants | 206 | 239 | 0 | 206 | — |
| | Products | 39 | — | 135 | 307 | 3 |

[a] = pressure measured for reactants at 50° C.;
[b] = pressure for water was calculated based on 4.3 g and assuming vaporation;
— = not detected Examples 5-8 show the products obtained when different starting compositions were tested. In Example 5, only $CO_2$ and $H_2$ were charged; both methanol and ethanol were produced. This may be compared with Example 6, in which only CO and $H_2$ were charged. Example 8 shows the negative influence of the presence of water on ethanol production. Examination of the product gases helps to explain this effect,

TABLE 3

| Reaction Time (min) | Gas-Phase Composition (mole %) | | |
|---|---|---|---|
| | CO | $H_2$ | $CO_2$ |
| heat up | 100.0 | tr | 0.0 |
| 0 | 89.7 | 5.5 | 4.9 |
| 15 | 82.8 | 8.3 | 8.9 |
| 30 | 65.6 | 12.8 | 21.6 |
| 60 | 29.3 | 32.2 | 38.5 |

TABLE 3-continued

| Reaction Time | Gas-Phase Composition (mole %) | | |
|---|---|---|---|
| (min) | CO | H$_2$ | CO$_2$ |
| 90 | 27.4 | 31.1 | 41.5 |
| 120 | 26.4 | 28.7 | 45.0 |
| 150 | 25.3 | 26.0 | 48.7 |
| 240 | 24.0 | 26.3 | 49.7 | tr = trace

Example 9 reveals the development of the RWGS equilibrium with the major change in carbon monoxide and carbon dioxide concentrations occurring in the first hour of a four-hour run.

Example 10, 12, and 14

Figure 5:
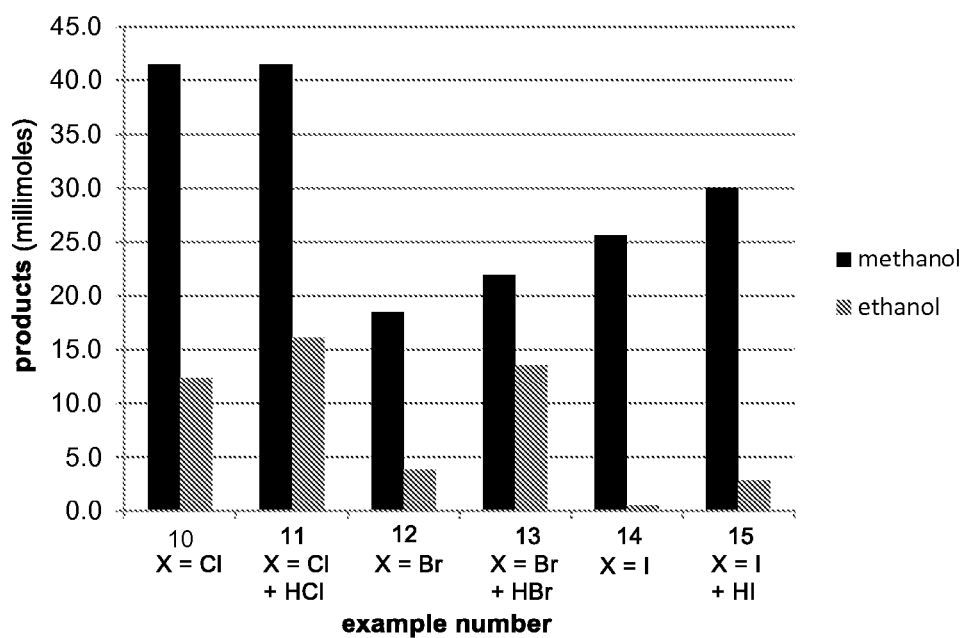
FIG. 5 is a bar graph of the amounts of methanol and ethanol produced in Examples 10-15. The x-axis shows the example numbers. The y-axis shows the amounts of methanol and ethanol in millimoles.

[PBu$_4$]X (44.2 mmol) and Ru3(CO)12 (0.250 g, 1.17 mmol of Ru) were added to the reactor (Example 10, X=Cl; Example 12, X=Br; Example 14, X=I). The reactor was purged and pressurized with syngas (17 MPa, CO:H$_2$=1:2). The system was heated to 200° C., and then the pressure was adjusted to 25 MPa. The reaction was allowed to stir for 4 hours under a constant pressure of 25 MPa, make-up CO/H$_2$ (1:1) being fed from a ballast vessel before the heating was switched off. Next, the reactor was allowed to cool to below 30° C., and the excess gas was vented. The red liquid product was distilled to yield the products. GC analysis was performed to determine the amount of methanol and ethanol produced by these compositions. The results are reported graphically in FIG. 5.

Examples 11, 13, and 15

Using the procedure described in Example 10, [PBu$_4$]X (44.2 mmol), conc. aq. HX (0.87 mmol), and Ru$_3$(CO)$_{12}$ (0.124 g, 1.17 mmol of Ru) were added to the reactor (Example 11, X=Cl; Example 13, X=Br; Example 15, X=I). The reactor charged was with 25 MPa 1:2 CO/H$_2$, heated to 200° C. for 4 hours, cooled below 30° C. GC analysis was performed to determine the amount of methanol and ethanol produced by these compositions. The results are reported graphically in FIG. 5.

The invention has been described in detail with particular reference to preferred embodiments thereof, but it will be understood that variations and modifications can be effected within the spirit and scope of the invention.

We claim:

1. A process for preparing methanol and ethanol, comprising:
   contacting a mixture of carbon dioxide and hydrogen with a catalyst system comprising a ruthenium compound and a chloride or bromide-containing compound dispersed in a low-melting tetraorganophosphonium chloride or bromide salt under conditions effective to produce methanol and ethanol,
   wherein the chloride or bromide-containing compound is selected from the group consisting of chlorine, bromine, hydrogen chloride, hydrogen bromide, alkyl chloride, alkyl bromide, and a triorganophosphonium salt.

2. The process according to claim 1, wherein the contacting step is carried out in the presence of methanol.

3. The process according to claim 1, wherein the mixture further comprises carbon monoxide.

4. The process according to claim 1, wherein the conditions effective to produce methanol and ethanol comprise a total pressure of 7 MPa to 25 MPa and a temperature of 150° C. to 220° C.

5. The process according to claim 1, wherein the ruthenium compound is selected from the group consisting of ruthenium oxide, ruthenium chloride, ruthenium bromide, anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium (III) acetylacetonate, triruthenium dodecacarbonyl, bis[ruthenium(tricarbonyl)dichloride], and bis[ruthenium(tricarbonyl)dibromide].

6. The process according to claim 1, wherein the chloride or bromide-containing compound is present in an amount sufficient to produce a Cl or Br-containing compound to Ru atom molar ratio of 0.2:1 to 0.8:1.

7. The process according to claim 1, wherein the chloride or bromide-containing compound is hydrogen chloride or hydrogen bromide.

8. The process according to claim 1, wherein the chloride or bromide-containing compound is a triorganophosphonium salt having the general formula (II):

$$[R_1R_2R_3PH][X^2] \quad\quad (II)$$

wherein
R$_1$, R$_2$, and R$_3$ are each independently selected from C$_1$-C$_{24}$ alkyl or aryl hydrocarbon groups or functionalized alkyl or aryl groups containing ether, alcohol, ketone, carboxylic acid or ester, amine, amide, thioether, phosphine oxide, nitrile, heteroaromatic, or fluorocarbon groups; and
X$^2$ is chloride or bromide.

9. The process according to claim 8, wherein X$^2$ is chloride.

10. The process according to claim 8, wherein the triorganophosphonium salt is tributylphosphonium chloride.

11. The process according to claim 10, wherein the molar ratio of the triorganophosphonium salt to Ru atom ranges from 0.2:1 to 0.6:1.

12. The process according to claim 1, wherein the tetraorganophosphonium salt has the general formula (I):

$$[R_1R_2R_3R_4P][X^1] \quad\quad (I)$$

wherein
R$_1$, R$_2$, R$_3$, and R$_4$ are each independently selected from C$_1$-C$_{24}$ alkyl or aryl hydrocarbon groups or functionalized alkyl or aryl groups containing ether, alcohol, ketone, carboxylic acid or ester, amine, amide, thioether, phosphine oxide, nitrile, heteroaromatic, or fluorocarbon groups; and
X$^1$ is chloride or bromide.

13. The process according to claim 12, wherein X$^1$ is chloride.

14. The process according to claim 12, wherein the tetraorganophosphonium salt is tetrabutylphosphonium chloride.

15. The process according to claim 3, wherein the volumetric ratio of carbon monoxide to carbon dioxide is from 0.01:1 to 100:1.

16. The process according to claim 1, wherein the volumetric ratio of carbon dioxide to hydrogen is from 0.1:1 to 1:1.

17. A process for preparing methanol and ethanol, comprising:
   contacting a mixture of carbon monoxide and water with a catalyst system comprising a ruthenium compound and a chloride or bromide-containing compound dispersed in a low-melting tetraorganophosphonium chloride or bromide salt under conditions effective to produce methanol and ethanol.

18. The process according to claim 17, wherein the contacting step is carried out in the presence of methanol.

19. The process according to claim 17, wherein the contacting step is carried out in the absence of hydrogen.

20. The process according to claim 17, wherein the conditions effective to produce methanol and ethanol comprise a total pressure of 7 MPa to 25 MPa and a temperature of 150° C. to 220° C.

21. The process according to claim 17, wherein the ruthenium compound is selected from the group consisting of ruthenium oxide, ruthenium chloride, ruthenium bromide, anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate, triruthenium dodecacarbonyl, bis[ruthenium(tricarbonyl)dichloride], and bis[ruthenium(tricarbonyl)dibromide].

22. The process according to claim 17, wherein the chloride or bromide-containing compound is hydrogen chloride or hydrogen bromide.

23. The process according to claim 17, wherein the chloride or bromide-containing compound is a triorganophosphonium salt having the general formula (II):

$$[R_1R_2R_3PH][X^2] \tag{II}$$

wherein
$R_1$, $R_2$, and $R_3$ are each independently selected from $C_1$-$C_{24}$ alkyl or aryl hydrocarbon groups or functionalized alkyl or aryl groups containing ether, alcohol, ketone, carboxylic acid or ester, amine, amide, thioether, phosphine oxide, nitrile, heteroaromatic, or fluorocarbon groups; and
$X^2$ is chloride or bromide.

24. The process according to claim 17, wherein the tetraorganophosphonium salt has the general formula (I):

$$[R_1R_2R_3R_4P][X^1] \tag{I}$$

wherein
$R_1$, $R_2$, $R_3$, and $R_4$ are each independently selected from $C_1$-$C_{24}$ alkyl or aryl hydrocarbon groups or functionalized alkyl or aryl groups containing ether, alcohol, ketone, carboxylic acid or ester, amine, amide, thioether, phosphine oxide, nitrile, heteroaromatic, or fluorocarbon groups; and
$X^1$ is chloride or bromide.

* * * * *